United States Patent
Nakashimada et al.

(10) Patent No.: US 6,533,823 B2
(45) Date of Patent: Mar. 18, 2003

(54) DYE COMPOSITION FOR KERATINOUS FIBERS

(75) Inventors: Atsushi Nakashimada, Sumida-Ku (JP); Masaki Fukuhara, Sumida-Ku (JP)

(73) Assignee: KAO Corporation, Tokyo (JP)

(*) Notice: Subject to any disclaimer, the term of this patent is extended or adjusted under 35 U.S.C. 154(b) by 0 days.

(21) Appl. No.: 09/798,819

(22) Filed: Mar. 5, 2001

(65) Prior Publication Data

US 2001/0029637 A1 Oct. 18, 2001

(30) Foreign Application Priority Data

Mar. 16, 2000 (JP) ........................................ 2000-074346

(51) Int. Cl.$^7$ ................................................ A61K 7/13
(52) U.S. Cl. ........................ 8/405; 8/405; 8/406; 8/409; 8/455; 8/557; 424/47; 424/61; 424/70; 424/78; 424/80; 524/401; 526/271; 526/216; 526/332; 526/336; 526/272
(58) Field of Search ................................ 526/271, 216, 526/332, 336, 272; 524/401; 8/404, 405, 406, 409, 407, 455, 557; 424/47, 61, 70, 78, 80

(56) References Cited

U.S. PATENT DOCUMENTS

| | | | |
|---|---|---|---|
| 4,445,521 A | * 5/1984 | Grollier et al. ................. | 132/7 |
| 4,719,099 A | * 1/1988 | Grollier et al. ................. | 424/47 |
| 4,898,725 A | * 2/1990 | Hoeffkes et al. ............... | 424/70 |
| 5,188,820 A | * 2/1993 | Cummins et al. ............. | 424/49 |
| 5,254,333 A | * 10/1993 | Kajino et al. ................. | 424/70 |
| 5,536,039 A | 7/1996 | Kwak et al. .................. | 524/401 |
| 5,874,510 A | 2/1999 | Kwak et al. .................. | 526/271 |
| 5,879,669 A | 3/1999 | Clausen et al. .......... | 424/70.11 |

FOREIGN PATENT DOCUMENTS

EP  0 784 970  7/1997
EP  1 157 684  11/2001

OTHER PUBLICATIONS

International Cosmetic Ingredient Dictionary and Handbook, ninth edition 2002, vol. 2, PVM/MA Decadiene Crosspolymer "Stabalize QM", Monographs, p. 1433.
International Specialty Products, Performance Enhancing Products for Personal Care w/ English Translation, "Stabileze® 06 & QM", printed 1998.
ISP: Reference Guide for Personal Care, Online, Retrieved from the Internet: <URL:http://208.240.92.118/products/hairskin/skincare/care_ref.html>, pp. 1–31, XP–002182444, "Skin Care", 1999.
Research Disclosure, vol. 343, pp. 879–887, "PVM/MA Decadiene Crosspolymer: a New Thickener/Stabilizer", Nov. 1, 1992.
Patent Abstracts of Japan, JP 11–130639, May 18, 1999.

* cited by examiner

*Primary Examiner*—Mark Kopec
*Assistant Examiner*—Eisa Elhilo
(74) *Attorney, Agent, or Firm*—Oblon, Spivak, McClelland, Maier & Neustadt, P.C.

(57) ABSTRACT

Provided is a dye composition for keratinous fibers, which comprises (A) a hydrolyzate of a lower alkyl vinyl ether/ maleic anhydride copolymer partially crosslinked with a terminal unsaturated diene compound, or a monoalkyl ester of the hydrolyzate; and (B) a dye.

The dye composition for keratinous fibers according to the present invention has a stable and appropriate viscosity even in a wide pH range and even in a system containing a salt or solvent at a high concentration; and has excellent usability and dyeing properties. It is particularly suited for use with an acid dye.

43 Claims, No Drawings

DYE COMPOSITION FOR KERATINOUS FIBERS

BACKGROUND OF THE INVENTION

1. Field of the Invention

The present invention relates to a dye composition for keratinous fibers, which exhibits a stable and appropriate viscosity in a wide pH range and even in a system containing a salt or solvent at a high concentration, is excellent in usability and dyeing properties and is particularly suited for use with an acid dye.

2. Description of the Related Art

It is the common practice to incorporate, in a dye composition for keratinous fibers such as hair dye, a thickener with a view toward preventing liquid dripping, thereby improving handling use of it or improving retention of the dye in keratinous fibers. As such a thickener, natural polymers such as xanthan gum and guar gum, and semi-synthetic polymers such as methyl cellulose and hydroxyethyl cellulose are employed by way of example.

In a dye composition, an acid dye, basic dye, oxidation dye or the like is contained as a dye. Suitable pH conditions are necessary for effective staining of keratinous fibers with this dye. For example, keratinous fibers are dyed well with an acid dye at a pH in the vicinity of 1.5 to 5, and with an oxidation dye at a pH in the vicinity of 6 to 10. Thus, it is necessary to adjust the pH to fall within a wide range, depending on the kind of a dye.

In general, however, a thickener exhibits good thickening effects within a limited pH range and many thickeners lack in stability at a low pH. Xanthan gum or the like is known as a thickener rather free from the influence of pH. Xanthan gum was however accompanied with the problems that owing to insufficient fluidity of a dye composition containing it, the composition dripped as a mass when applied to the hair by hands or some tool. In addition, the dye composition containing xanthan gum involved problems in usability, that is, low spreadability over the hair and in dyeing properties. Thus, a dye composition containing an acid dye conventionally used within a particularly low pH range was not sufficient in usability and dyeing properties.

An object of the present invention is therefore to provide a dye composition for keratinous fibers which composition exhibits a stable and appropriate viscosity in a wide pH range and even in a system containing a salt or solvent at a high concentration, and is excellent in usability and dyeing properties.

SUMMARY OF THE INVENTION

The present inventors have found that a dye composition for keratinous fibers which can satisfy the above-described object is available by incorporating therein a specific anionic partially crosslinked polymer.

In the present invention, there is thus provided a dye composition for keratinous fibers, which comprises the following components (A) and (B):

(A) a hydrolyzate of a lower alkyl vinyl ether/maleic anhydride copolymer partially crosslinked with a terminally unsaturated diene compound, or a monoalkyl ester of the hydrolyzate; and (B) a dye.

The dye composition for keratinous fibers according to the present invention has a stable and appropriate viscosity in a wide pH range and even in a system containing a salt or solvent at a high concentration; and has excellent usability and dyeing properties. It is particularly suited for use with an acid dye.

DETAILED DESCRIPTION OF THE PREFERRED EMBODIMENTS

The lower alkyl vinyl ether/maleic anhydride copolymer partially crosslinked by a terminally unsaturated diene compound (which copolymer will hereinafter be called "partially crosslinked polymer", simply), one of the components to be used in the present invention, is as described in U.S. Pat. No. 5,539,039 and U.S. Pat. No. 5,874,510. By the hydrolysis of it, the hetero ring of maleic anhydride becomes a dicarboxylic acid, whereby a colorless transparent gel is formed.

Examples of the lower alkyl group of the lower alkyl vinyl ether to be used for the partially crosslinked polymer include $C_{1-4}$ alkyl groups. Among them, methyl and ethyl groups are preferred, with methyl group being particularly preferred.

The molar ratio of the lower alkyl vinyl ether to maleic anhydride in the partially crosslinked polymer ranges from 40:60 to 60:40, with a range of from 45:55 to 55:45 being particularly preferred.

Examples of the terminally unsaturated diene compound to be used as a crosslinking agent include $C_{6-18}$ compounds such as 1,5-hexadiene, 1,7-octadiene, 1,9-decadiene, 1,11-dodecadiene, 1,15-hexadecadiene, divinylbenzene, ethylene dimethacrylate, methacrylic anhydride and diaryl phthalate. Among them, terminally unsaturated alkadienes are preferred, with 1,9-decadiene being particularly preferred.

The crosslinking degree of the partially crosslinked polymer by the above-described crosslinking agent is preferred to be 1 to 5%, especially 2 to 4% and its average molecular weight is preferably at least 1,000,000.

Such a partially crosslinked polymer is available as a uniform suspension by polymerizing a lower alkyl vinyl ether and maleic anhydride in a proper solvent in the presence of a crosslinking agent (a terminal unsaturated diene compound) and a polymerization initiator at 60 to 80° C. As the solvent and polymerization initiator, isopropyl acetate an the like, and 2,2'-azobis (2-methylbutanenitrile), decanoyl peroxide and the like can be used, respectively.

As the partially crosslinked polymer, commercially available products can also be employed. Examples include "Stabileze 06" and "Stabileze QM" (each, trade name; product of ISP Inc.), that is, a methyl vinyl ether/maleic anhydride copolymer partially crosslinked with 1,9-decadiene.

As described above, by the hydrolysis to convert the hetero ring of maleic anhydride into a dicarboxylic acid, the partially crosslinked polymer forms a colorless transparent gel. This hydrolysis is effected in a manner known per se in the art, for example, by dispersing the polymer in water and then heating. The partially crosslinked polymer wherein the dicarboxylic acid has partially been monoalkyl esterified is also usable and in this case, $C_{1-4}$ alkyl groups are preferred as the alkyl group. Esterification can be conducted, for example, by reacting the partially crosslinked polymer with a lower alcohol corresponding to the alkyl group in a solvent such as acetone. A desired viscosity is available by neutralizing the hydrolyzate or monoalkyl ester thereof with an alkali as needed.

Examples of the alkali usable for neutralization include inorganic alkali agents such as sodium hydroxide and potassium hydroxide; organic alkali agents such as monoethanolamine, diethanolamine, triethanolamine and aminopropanol; ammonia: carbonates such as ammonium carbonate, potassium carbonate, sodium carbonate and guanidine carbonate; basic amino acids such as arginine. Among them, alkali metal hydroxides are preferred.

The content of Component (A) in the dye composition for keratinous fibers according to the present invention is preferably 0.1 to 15 wt. %, with 0.5 to 10 wt. % being particularly preferred.

As the dye [Component (B)] to be used in the present invention, preferred are acid dyes, basic dyes, nonionic dyes and oxidation dyes, with acid dyes being particularly preferred.

Examples of the acid dye include Acid Red 27 (C.I. 16185), Acid Red 51 (C.I.45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87(1) (C.I. 45380), Acid Red 92 (C.I. 45410), Acid Red 94 (C.I. 45440), Acid Orange 7 (C.I. 15510), Acid Red 95 (C.I. 45425), Acid Yellow 73 (C.I. 45350), Acid Yellow 3 (C.I. 47005), Acid Green 25 (C.I. 61570), Acid Green 5 (C.I. 42095), Acid Blue 5 (C.I. 42052), Acid Blue 9 (C.I. 42090), Acid Orange 24 (C.I. 20170), Acid Violet 9 (C.I. 45190), Food Red 6 (C.I. 16155), Acid Red 26 (C.I. 16150), Food Red 1 (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685) and Brilliant Black 1 (C.I. 28440).

Examples of the basic dye include Basic Blue 7 (C.I. 42595), Basic Blue 26 (C.I.44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1), Basic Yellow 57 (C.I. 12719), basic dyes, as described in Japanese Patent Publication No. 2204/1983 and Japanese Patent Application Laid-Open No. 118832/1997, which contain, at the side chain of the aromatic ring thereof, a quaternized nitrogen atom, and basic dyes, as described in Japanese-Language Laid-Open Publication (PCT) No. 502946/1998 and Japanese Patent Application Laid-Open No. 182379/1998, which are represented by the below-described formula and contain a quaternized nitrogen atom which may be non-localized and a —Z=N— bond (Z represents a nitrogen atom or a group —CH=).

Examples of the nonionic dyes include so called nitro dyes, such as those as described in U.S. Pat. No. 4,834,768, from line 65 of the second column to line 31 of the third column.

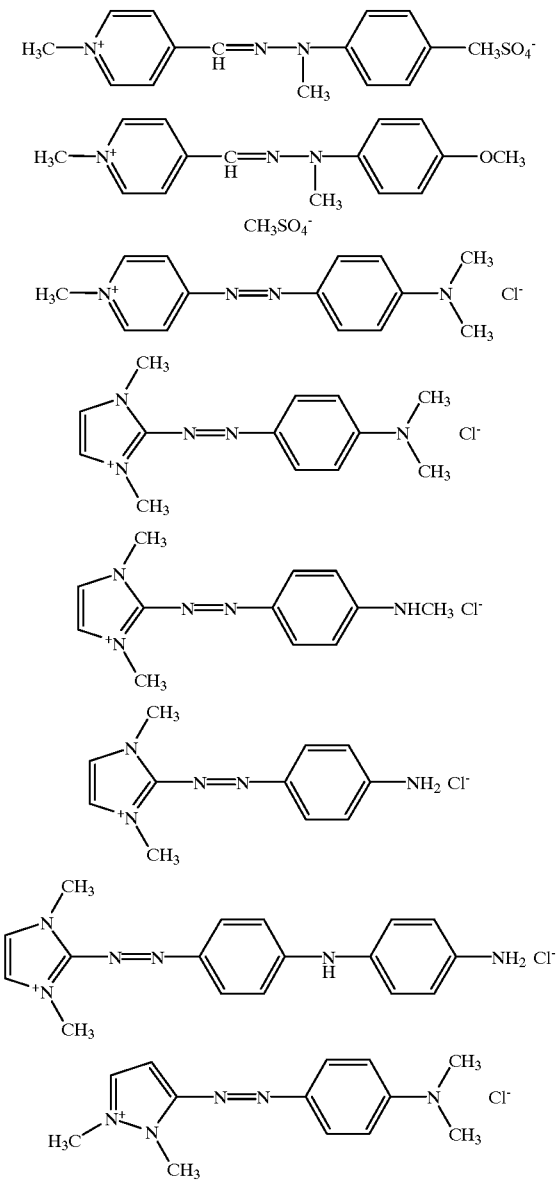

It is preferred to incorporate the above-exemplified acid dye or basic dye to the dye composition of the present invention in an amount of 0.01 to 10 wt. %, more preferably 0.01 to 5 wt. %, especially 0.05 to 3 wt. % based on the whole composition.

Addition of a solvent as a penetration promoter is preferred when an acid dye or basic dye is employed. Examples of such a solvent include $C_{1-6}$-alkyl-containing monohydric alcohols such as ethanol, 1-propanol, 2-propanol, 1-butanol and 2-butanol; $C_{6-6}$ alcohols having at least two hydroxyl groups or ethers thereof such as propanediol, butanediol, pentanediol, hexanediol, hexanetriol, heptanediol, heptanetriol, octanediol, octanetriol, isopreneglycol, propyleneglycol, glycerin, diethylene glycol monoethyl ether, diethylene glycol diethyl ether and ethylene glycol monoethyl ether; N-alkylpyrrolidones which are liquid at normal temperature such as N-methyl-2-pyrrolidone, N-ethyl-2-pyrrolidone, N-propyl-2-pyrrolidone, N-butyl-2-pyrrolidone and N-cyclohexyl-2-pyrrolidone; lower alkylene carbonates such as ethylene carbonate and propylene carbonate; and aromatic alcohols such as benzyl alcohol, benzyloxy ethanol, cinnamyl alcohol, p-anisyl alcohol, p-methylbenzyl alcohol, phenoxyethanol, phenoxy isopropanol, 2-benzylethanol and β-phenylethyl alcohol. Among them, aromatic alcohols, lower alkylene carbonates, N-alkyl pyrrolidones are preferred, with benzyl alcohol, benzyloxy ethanol and propylene carbonate being particularly preferred. These solvents may be used either singly or in combination. The solvent is preferably added in an amount of 0.1 to 60 wt. % to the dye composition of the present invention.

When an oxidation dye is employed, an intermediate for the oxidation dye can be used in combination for the formulation of a first hair dye component. As the intermediate for the oxidation dye, a developer and coupler are employed.

Examples of the developer include —NH$_2$—, —NHR— or —NR$_2$-containing p-phenylenediamines (R represents a C$_{1-4}$ alkyl or hydroxyalkyl group) such as p-phenylenediamine, p-toluylenediamine, N-methyl-p-phenylenediamine, N,N-dimethyl-p-phenylenediamine, N,N-diethyl-2-methyl-p-phenylendiamine, N-ethyl-N-(hydroxyethyl)-p-phenylenediamine, chloro-p-phenylenediamine, 2-(2'-hydroxyethylamino)-5-aminotoluene, N,N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxy-propyl)-p-phenylenediamine and N-2-methoxyethyl-p-phenylenediamine; 2,5-diaminopyridine derivatives; and p-aminophenols, o-aminophenols and o-phenylenediamines such as p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2,4-diaminophenol and 5-aminosalicylic acid.

Examples of the coupler include α-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, 5-(2'-hydroxyethylamino)-4-methoxyphenol, hydroquinone, 2,4-diaminoanisole, m-toluylenediamine, 4-aminophenol, resorcin, resorcin monomethyl ether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxy-2-quinolone, m-aminophenol, 4-chlororesorcinol, 2-methylresorcinol, 2,4-diaminophenoxyethanol, 2,6-diaminopyridine, 3,5-diaminotrifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxypyrimidine and 4,6-diamino-2-hydroxypyrimidine.

As the developer or coupler, at least one of the above-exemplified ones may be used. It is preferably added in an amount of 0.01 to 20 wt. %, especially 0.5 to 10 wt. % based on the whole composition.

As the pH of the dye composition of the present invention, preferred is 1.5 to 5, especially 2 to 4 and more preferably 2.5 to 4 when an acid dye is employed as a dye; preferred is 5 to 14, especially 8 to 10 when a basic dye is employed; or preferred is 6 to 14, especially 8 to 10 when an oxidation dye is employed. This pH value is that of the stock solution of the dye composition measured without dilution. The dye composition of the present invention has a viscosity appropriate for dyeing operation and exhibits excellent dyeing properties even within the above-described pH range.

Examples of an acid to be used for pH adjustment include organic acids and salts thereof such as succinic acid, malonic acid, maleic acid, fumaric acid, citric acid, maleic acid, acetic acid, lactic acid, oxalic acid, tartaric acid, formic acid, glycolic acid, levulinic acid and isethionic acid and salts thereof; and inorganic acid such as phosphoric acid and hydrochloric acid. Among them, citric acid, lactic acid, glycolic acid and levulinic acid are preferred. Examples of the alkali agent include inorganic alkali agents such as sodium hydroxide and potassium hydroxide; organic alkali agents such as monoethanolamine, diethanolamine, triethanolamine and aminopropanol; ammonia; ammonium chloride; carbonates such as ammonium carbonate, potassium carbonate, sodium carbonate and guanidine carbonate; and basic amino acids such as arginine. Among them, alkali metal hydroxides are preferred.

To the dye composition of the present invention, a thickener other than Component (A) can be added. Examples of such a thickener include carboxyvinyl polymer, alkyl-modified carboxyvinyl polymer, gum arabic, carrageenan, Karaya gum, tragacanth gum, wellan gum, carob gum, Gum Quince seed (quince), casein, dextrin, gelatin, sodium pectate, sodium alginate, methyl cellulose, ethyl cellulose, carboxymethyl cellulose, hydroxyethyl cellulose, hydroxypropyl cellulose, polyvinyl alcohol, polyvinyl methyl ether, polyvinyl pyrrolidone, sodium polyacrylate, polyacrylic amide, locust bean gum, guar gum, tamarind gum, cellulose dialkyldimethylammonium sulfate, xanthan gum, aluminum magnesium silicate and bentonite.

In addition to the above-described components, components ordinarily employed for cosmetics can be incorporated in the dye composition of the present invention as needed. Examples include surfactants, cationic polymers, lower alcohols, polyols, oil components, silicone derivatives, pigments, chelating agents, perfumes, antiseptics, ultraviolet absorbers, antioxidants, bactericides and propellants. The dye composition of the present invention can be prepared in a conventional manner. The dye composition of the present invention can be prepared in any form such as transparent liquid, emulsion, cream, gel, paste or mousse.

As the keratinous fibers to which the dye composition of the present invention is applied, hair is preferred.

EXAMPLES

Examples 1 and Comparative Examples 1 to 8

Dye compositions (acid dye, pH 2.8) shown in Table 1 were prepared and usability, dyeing properties and stability of them were evaluated. The results are shown in Table 1.
(Preparation Process)

(1) Example 1

To Component (17) added were Components (4) to (6) and Component (15). Component (7) was then added to the resulting mixture, followed by stirring. The reaction mixture was heated to 80° C. and then stirred for about 1 hour without changing the temperature. Heating was terminated when the mixture became a viscous solution and the resulting solution was allowed to cool down to room temperature.

When the temperature of the solution decreased to 40° C. or less, Components (1), (3) and (16) were added and the resulting mixture was stirred for about 30 minutes, whereby a viscous solution was obtained.

(2) Comparative Examples 1–8

To component (17) were added Components (3) to (6) and (15), followed by stirring. To the resulting mixture was added a polymer-dispersed solution obtained in advance by adding one component selected from Components (8) to (14) to Components (1), (2) and (16). The resulting mixture was stirred for 1 hour at room temperature, whereby a viscous solution was obtained.

(Evaluation Methods and Standards)
(1) Adhesion to Hair

A double-side tape of about 4 cm in total length was adhered onto a slide glass along a longer direction thereof. At intervals of 1 to 1.5 mm, sets of two hairs were laid thereover so that the distance from the first set to the last set would be 3 cm and the length of the hairs protruded outside the slide grass would be about 5 cm. Another slide glass was stacked thereover. This operation was repeated twice further, whereby a test tress having three hair layers was formed.

About 0.35 g of a dye composition was applied five times to the hairs (5 cm) outside the slide glass of this tress by using a comb (3.5 cm in total length, distance between comb teeth: 1 mm, length of the comb tooth: 6 mm). Application was started from the edge of the slide glass toward the tip of the hairs. Spans from the edge of the slide glass to the points at which mutual adhesion of hairs by the dye composition was observed (non-adhered portion), as well as a weight change of the test tress before and after the application of the dye composition, were measured. The higher the adhesion to hair, the shorter the non-adhered portion and the greater a weight change of the test tress.

(2) Dyeing Properties

Ten females having a white hair rate (percentage of white hair in the whole hair) of about 10 to 30% were asked to evaluate the dyeing properties in accordance with the below-described standards. The judgment was made based on the average.

Satisfactory: 5 points
Slightly satisfactory: 4 points
Difficult to evaluate: 3 points
Slightly unsatisfactory: 2 points
Unsatisfactory: 1 point Judgment
A: 4.5 points or greater in average
B: 3.5 to 4.4 points on average
C: 2.5 to 3.4 points on average
D: 2.4 points or less on average (3) Storage Stability The appearance of each of the dye compositions stored at −5° C. and 50° C. for one week was visually evaluated in accordance with the following standards:
A: no change before and after storage
B: separation occurred

TABLE 1

| | | Ex. | Comparative Examples | | | | | | | |
|---|---|---|---|---|---|---|---|---|---|---|
| | | 1 | 1 | 2 | 3 | 4 | 5 | 6 | 7 | 8 |
| (1) | Benzyl alcohol | 10 | 10 | 10 | 10 | 10 | 10 | 10 | 10 | 10 |
| (2) | Propylene carbonate | — | — | — | — | — | — | — | 10 | 10 |
| (3) | Ethanol | 10 | 10 | 10 | 10 | 10 | 10 | 10 | 5 | 5 |
| (4) | Sodium hydroxide | q.s. | q.s. | q.s. | q.s. | q.s. | q.s. | q.s. | q.s. | q.s. |
| (5) | Lactic acid | 4.5 | 4.5 | 4.5 | 4.5 | 4.5 | 4.5 | 4.5 | 4.5 | 4.5 |
| (6) | Acid Orange 7 | 0.5 | 0.5 | 0.5 | 0.5 | 0.5 | 0.5 | 0.5 | 0.5 | 0.5 |
| (7) | Stabileze QM (product of ISP) | 3 | — | — | — | — | — | — | — | — |
| (8) | Xanthan gum *1 | — | 3 | — | — | — | — | — | — | — |
| (9) | Hydroxyethyl cellulose*2 | — | — | 3 | — | — | — | — | — | — |
| (10) | Hydroxypropyl cellulose*3 | — | — | — | 3 | — | — | — | — | — |
| (11) | Hydroxypropyl guar gum *4 | — | — | — | — | 3 | — | — | — | — |
| (12) | Propylene glycol alginate *5 | — | — | — | — | — | 3 | — | — | — |
| (13) | Acrylic acid - alkyl methacrylate copolymer A *6 | — | — | — | — | — | — | 3 | 3 | — |
| (14) | Acrylic acid - alkyl methacrylate copolymer B *7 | — | — | — | — | — | — | — | — | 3 |
| (15) | Edatate disodium | 0.1 | — | — | — | — | — | 0.1 | 0.1 | 0.1 |
| (16) | Perfume | 0.1 | 0.1 | 0.1 | 0.1 | 0.1 | 0.1 | 0.1 | 0.1 | 0.1 |
| (17) | water | Balance | Balance | Balance | Balance | Balance | Balance | Balance | Balance | Balance |
| Adhesion to Hair | Distance of non-adhered portion (mm) | 2 | 12 | 7 | 9 | 8 | 5 | 5 | 4 | 6 |
| | Weight change (mg) | 211 | 52 | 87 | 179 | 93 | 170 | 156 | 172 | 177 |
| Dyeing Properties | Dyeing effects | A | C | B | B | C | C | A | A | B |
| | Fastness to hair washing | A | C | B | B | C | C | A | A | B |
| Storage Stability | at 50° C. for 1 week | A | B | B | B | B | B | A | A | A |
| | at 50° C. for 1 week | A | A | A | A | A | A | B | B | B |

*1"Echo Gum T" (trade name; product of Dainippon Pharmaceutical Co., Ltd.)
*2"HEC Daicel SE850" (trade name; product of Daicel Chemical Industries, Ltd.)
*3"Metolose 60SH1000" (trade name; product of Shin-Etsu Chemical Co., Ltd.)
*4"Jaguar HP-60" (trade name; product of Sansho Co., Ltd.)
*5"Kimileudo HV" (trade name; product of Kimitsu Chemical Industries Co., Ltd.)
*6"Carbopol ULTREZ10" (trade name; product of B. F. Goodrich Company)
*7"Carbopol ETD2020" (trade name; product of B. F. Goodrich Company)

Example 2

Dye Composition

| (Composition) | (wt. %) |
|---|---|
| Benzyl alcohol | 5 |
| Ethanol | 10 |
| Sodium hydroxide | q.s. |
| Lactic acid | 4.5 |
| Acid Orange 7 | 0.5 |
| Edatic acid | 0.1 |
| "Stabileze QM" (trade name; product of ISP) | 3 |
| Perfume | 0.1 |
| Water | Balance |

(Preparation Process)

To purified water were added sodium hydroxide, Orange No. 205 and edatic acid. To the resulting mixture was added "Stabileze QM" and they were stirred. The solution was heated to 80° C. and stirred for about 1 hour without changing the temperature. Heating was terminated when the reaction mixture became a viscous solution. The solution was allowed to cool down to room temperature. When the temperature of the solution decreased 40° C. or less, benzyl alcohol, ethanol and perfume were added. The mixture was stirred for about 30 minutes, whereby a dye composition (pH 2.8) was obtained as a viscous solution.

Example 3

Dye Composition

A dye composition (pH 2.8) was prepared in accordance with Example 2.

| (Composition) | (wt. %) |
|---|---|
| Benzyl alcohol | 5 |
| Dipropylene glycol | 15 |
| Sodium hydroxide | q.s. |
| Citric acid | 4 |
| Acid Orange 7 | 0.4 |
| Acid Black 1 | 0.2 |
| Acid Violet 43 | 0.1 |
| Dimethylpolysiloxane ("Silicone KF9GH-5000cs", product of Shinetsu Chemical) | 1.5 |
| Edatate disodium | 0.1 |
| "Stabileze QM" (trade name; product of ISP) | 3 |
| Perfume | 0.1 |
| Water | Balance |

Example 4

Dye Composition

A dye composition (pH 2.8) was prepared in accordance with Example 2.

| (Composition) | (wt. %) |
|---|---|
| Benzyloxy ethanol | 3 |
| Dipropylene glycol | 10 |
| Sodium hydroxide | q.s. |
| Glycolic acid | 3 |
| Acid Orange 7 | 0.4 |
| Acid Black 1 | 0.2 |
| Acid Violet 43 | 0.1 |
| Polyether-modified silicone ("Silicone KF352A", product of Shinetsu Chemical) | 1.5 |
| Edatate tetrasodium | 0.1 |
| "Stabileze QM" (trade name; product of ISP) | 3 |
| Perfume | 0.1 |
| Water | Balance |

Example 5

Dye Composition

A dye composition (pH 2.8) was prepared in accordance with Example 2.

| (Composition) | (wt. %) |
|---|---|
| Benzyl alcohol | 5 |
| Propylene carbonate | 10 |
| Polyethylene glycol 400 | 5 |
| Sodium hydroxide | q.s. |
| Lactic acid | 5 |
| Acid orange 7 | 0.4 |
| Acid Black 1 | 0.2 |
| Acid Violet 43 | 0.1 |
| Amino-modified silicone ("Silicone SM-8702c", product of Toray Dow Coning) | 1.5 |
| Edatate tetrasodium | 0.1 |
| "Stabileze QM" (trade name; product of ISP) | 3 |
| Perfume | 0.1 |
| Water | Balance |

Example 6

Dye Composition

A dye composition (pH 2.8) was prepared in accordance with Example 2.

| (Composition) | (wt. %) |
|---|---|
| Benzyl alcohol | 3 |
| N-methylpyrrolidone | 3 |
| Dipropylene glycol | 5 |
| Ethanol | 4 |
| Sodium hydroxide | q.s. |
| Lactic acid | 4 |
| Acid Orange 7 | 0.4 |
| Acid Black 1 | 0.2 |
| Acid Violet 43 | 0.1 |
| Amino-modified silicone ("Silicone SM-8702c", product of Toray Dow Coning) | 1 |
| Edatate disodium | 0.1 |
| "Stabileze QM" (trade name; product of ISP) | 3 |
| Perfume | 0.1 |
| Water | Balance |

Example 7

Dye Composition

A dye composition (pH 2.8) was prepared in accordance with Example 2.

| (Composition) | (wt. %) |
|---|---|
| Benzyloxy ethanol | 7 |
| N-methylpyrrolidone | 3 |
| Ethanol | 15 |
| Polyethylene glycol 400 | 3 |
| Sodium hydroxide | q.s. |
| Citric acid | 4 |
| Acid Orange 7 | 0.4 |
| Acid Black 1 | 0.2 |
| Acid Violet 43 | 0.1 |
| Edetic acid | 0.1 |
| "Stabileze QM" (trade name; product of ISP) | 3 |
| Polyvinylpyrrolidone ("Rubiscole K30", product of BASF) | 1 |
| Perfume | 0.1 |
| Water | Balance |

Example 8

Dye Composition

A dye composition (pH 2.8) was prepared in accordance with Example 2.

| (Composition) | (wt. %) |
|---|---|
| Benzyloxy ethanol | 5 |
| N-methylpyrrolidone | 3 |
| Ethanol | 10 |
| Polyethylene glycol 600 | 3 |
| Sodium hydroxide | q.s. |
| Citric acid | 4 |
| Acid orange 7 | 0.4 |
| Acid Black 1 | 0.2 |
| Acid Violet 43 | 0.1 |
| Edatate disodium | 0.1 |
| "Stabileze QM" (trade name; product of ISP) | 3 |
| Polyvinyl alcohol ("Gohsenol EG-25", product of Nippon Synthetic Chemical Industry Co., Ltd.) | 1 |
| Perfume | 0.1 |
| Water | Balance |

Example 9

Dye Composition

| (Composition) | (wt. %) |
|---|---|
| Basic Yellow 57 | 1 |
| Ethanol | 20 |
| Benzyl alcohol | 5 |
| Amino-modified silicone ("Silicone SM-8702c", trade name; product of Dow Corning Toray Silicone Co., Ltd.) | 0.5 |
| Monoethanolamine | 0.5 |
| Phosphoric acid | for adjustment of pH to 8.7 |
| "Stabileze QM" (trade name; product of ISP) | 1 |
| Perfume | 0.1 |
| Edatate disodium | 0.1 |
| Purified water | Balance |

(Preparation Process)

To purified water were added Basic Yellow 57 and edatate disodium. "Stabileze QM" was added to the resulting mixture and they were stirred. The resulting solution was heated to 80° C. and without changing the temperature, stirring was conducted for about 1 hour. Heating was terminated when the reaction mixture became a viscous solution. The solution was allowed to cool down to room temperature. When the solution became 40° C. or less, monoethanolamine, benzyl alcohol, ethanol, amino-modified silicone and perfume were added. Phosphoric acid was added to adjust the pH of the mixture to 8.7, followed by stirring for about 80 minutes, whereby a dye composition was prepared as a viscous solution.

Example 10

Dye Composition

| (Composition) | (wt. %) |
|---|---|
| Aqueous ammonia (28%) | 3 |
| Monoethanolamine | 0.5 |
| Toluene-2,5-diamine | 1.0 |
| Resorcin | 0.6 |
| Meta-aminophenol | 0.4 |
| Polyoxyethylene (40) cetyl ether | 3 |
| Polyoxyethylene (2) cetyl ether | 3.5 |
| Sodium sulfite | 0.5 |
| Ascorbic acid | 0.5 |
| Edatate tetrasodium | 0.1 |
| "Stabileze QM" (trade name; product of ISP) | 0.5 |
| Perfume | 0.1 |
| Purified water | Balance |
| Ammonium chloride | for adjustment of pH to 10 |

(Preparation Process)

To purified water were added toluene-2,5-diamine, resorcin, meta-aminophenol, polyoxyethylene (40) cetyl ether, polyoxyethylene (2) cetyl ether, sodium sulfite, ascorbic acid, edatate tetrasodium and Stabileze QM. The resulting mixture was heated to 80° C. When the reaction mixture became a uniformly viscous solution, aqueous ammonia, monoethanolamine and perfume were added. Ammonium chloride was added further to adjust the pH of the mixture to 10, whereby a dye composition was prepared as a viscous solution.

It has been understood that any one of the dye compositions obtained in Examples 2 to 10 had appropriate viscosity and therefore was excellent in adhesion to the hair and spreadability, was free from liquid dripping upon application and had excellent usability. In addition, it had excellent dyeing properties.

What is claimed is:

1. A dye composition for keratinous fibers, which comprises the following Components (A), (B) and (C), and has a pH of from 1.5 to 5, (A) a hydrolyzate of a lower alkyl vinyl ether/maleic anhydride copolymer partially crosslinked with a terminally unsaturated diene compound, or a monoalkyl ester of the hydrolyzate; and (B) an acidic dye, and (C) a solvent selected from the group consisting of $C_{1-6}$-alkyl-containing monohydric alcohols, $C_{3-8}$ alcohols having at least two hydroxyl groups, ethers of $C_{3-8}$ alcohols having at least two hydroxyl groups, N-alkylpyrrolidones which are liquid at room temperature, lower alkylene carbonates, benzyl alcohol, benzyloxy ethanol, cinnamyl alcohol, p-anisyl alcohol, p-methylbenzyl alcohol, phenoxyethanol, phenoxy isopropanol, 2-benzylethanol, phenylethyl alcohol and mixtures thereof.

2. A dye composition for keratinous fibers according to claim 1, wherein the partially crosslinked polymer as Component (A) is a methyl vinyl ether/maleic anhydride copolymer partially crosslinked with 1,9-decadiene.

3. The dye composition for keratinous fibers of claim 1, wherein said lower alkyl vinyl ether has from 1 to 4 carbon atoms.

4. The dye composition for keratinous fibers of claim 1, wherein said lower alkyl vinyl ether is methyl vinyl ether.

5. The dye composition for keratinous fibers of claim 1, wherein said copolymer has a lower alkyl vinyl ether/maleic anhydride molar ratio of from 40:60 to 60:40.

6. The dye composition for keratinous fibers of claim 1, wherein said terminally unsaturated diene compound has from 6 to 18 carbon atoms.

7. The dye composition for keratinous fibers of claim 1, wherein said terminally unsaturated diene compound is selected from the group consisting of 1,5-hexadiene, 1,7-octadiene, 1,9-decadiene, 1,11-dodecadiene, 1,15-hexadecadiene, divinyl benzene, ethylene dimethacrylate, methacrylic anhydride and diarylphthalate.

8. The dye composition for keratinous fibers of claim 1, wherein said hydrolyzate is obtained by reacting the maleic anhydride hetero ring with water to form a dicarboxylic acid.

9. The dye composition for keratinous fibers of claim 1, further comprising a thickener.

10. A process for preparing the dye composition for keratinous fibers of claim 1, said process comprising
adding said copolymer and said dye to water to form a mixture, then
heating said mixture to obtain said dye composition.

11. The dye composition for keratinous fibers of claim 1, wherein an ester group of said monoalkyl ester of said hydrolyzate contains from 1 to 4 carbon atoms.

12. The dye composition for keratinous fibers of claim 1, wherein said copolymer has an average molecular weight of at least 1,000,000.

13. The dye composition for keratinous fibers of claim 1, wherein said acid dye is present in an amount of from 0.01–10 wt. %.

14. The dye composition for keratinous fibers of claim 1, further comprising an acid adjuster.

15. The dye composition for keratinous fibers of claim 1, further comprising an additional component selected from the group consisting of a surfactant, a cationic polymer, a lower alcohol, a polyol, an oil component, a silicone derivative, a pigment, a chelating agent, a perfume, an antiseptic, an ultraviolet absorber, an antioxidant, a bacteriacide and a propellant.

16. The dye composition for keratinous fibers of claim 1, wherein said keratinous fibers are hair.

17. A method for dying, said method comprising
applying the dye composition of claim 1 to keratinous fibers.

18. The method according to claim 17, wherein the keratinous fibers are hair.

19. The method according to claim 17, wherein said lower alkyl vinyl ether has from 1 to 4 carbon atoms.

20. The method according to claim 17, wherein said lower alkyl vinyl ether is methyl vinyl ether.

21. The dye composition for keratinous fibers of claim 17, wherein said copolymer has a lower alkyl vinyl ether/maleic anhydride molar ratio of from 40:60 to 60:40.

22. The method according to claim 17, wherein said terminally unsaturated diene compound has from 6 to 18 carbon atoms.

23. The method according to claim 17, said terminally unsaturated diene compound is selected from the group consisting of 1,5-hexadiene, 1,7-octadiene, 1,9-decadiene, 1,11-dodecadiene, 1,15-hexadecadiene, divinyl benzene, ethylene dimethacrylate, methacrylic anhydride and diarylphthalate.

24. The method according to claim 17, wherein said hydrolyzate is obtained by reacting the maleic anhydride hetero ring with water to form a dicarboxylic acid.

25. The method according to claim 17, further comprising a thickener.

26. The method according to claim 17, wherein an ester group of said monoalkyl ester of said hydrolyzate contains from 1 to 4 carbon atoms.

27. The method according to claim 17, wherein said dye is selected from the group consisting of a basic dye, a nonionic dye and an oxidation dye.

28. The method according to claim 17, wherein said copolymer has an average molecular weight of at least 1,000,000.

29. The method according to claim 17, wherein said dye is an acid dye.

30. The method according to claim 29, wherein said acid dye is present in an amount of from 0.01–10 wt. %.

31. The method according to claim 17, further comprising a solvent.

32. The method according to claim 17, wherein said composition has a pH of from 1.5–5.

33. The method according to claim 17, further comprising an acid adjuster.

34. The method according to claim 17, further comprising an additional component selected from the group consisting of a surfactant, a cationic polymer, a lower (alcohol, a polyol, an oil component, a silicone derivative, a pigment, a chelating agent, a perfume, an antiseptic, an ultraviolet absorber, an antioxidant, a bacteriacide and a propellant.

35. The method according to claim 17, wherein the partially crosslinked polymer is a methyl vinyl ether/maleic anhydride copolymer partially crosslinked with 1,9-decadiene.

36. The dye composition for keratinous fibers of claim 1, wherein the composition comprises a solvent selected from the group consisting of ethanol, 1-propanol, 2-propanol, 1-butanol, 2-butanol, and mixtures thereof.

37. The dye composition for keratinous fibers of claim 1, wherein the composition comprises a solvent selected from the group consisting of propanediol, butanediol, pentanediol, hexanediol, hexanetriol, heptanediol, heptanetriol, octanediol, octanetriol, isopreneglycol, propyleneglycol, glycerin, diethylene glycol monoethyl ether, diethylene glycol diethyl ether, ethylene glycol monoethyl ether and mixtures thereof.

38. The dye composition for keratinous fibers of claim 1, wherein the composition comprises a solvent selected from the group consisting of N-methyl-2-pyrrolidone, N-ethyl-2-pyrrolidone, N-propyl-2-pyrrolidone, N-butyl-2-pyrrolidone, N-cyclohexyl-2-pyrrolidone and mixtures thereof.

39. The dye composition for keratinous fibers of claim 1, wherein the composition comprises a solvent selected from the group consisting of ethylene carbonate, propylene carbonate and mixtures thereof.

40. The dye composition for keratinous fibers of claim 1, comprising a solvent selected from the group consisting of benzyl alcohol, benzyloxy ethanol, propylene carbonate and mixtures thereof.

41. The dye composition for keratinous fibers of claim 1, wherein the solvent is present in an amount of from 0.1 to 60 weight %.

42. The dye composition for keratinous fibers of claim 1, wherein the pH is from 2 to 4.

43. The dye composition for keratinous fibers of claim 1, wherein the acidic dye is selected from the group consisting of Acid 27 (C.I. 16185), Acid Red 51 (C.I. 45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87(1) (C.I. 45380), Acid Red 92 (C.I. 45410), Acid Red 94 (C.I. 45440), Acid Orange 7 (C.I. 15510), Acid Red 95 (C.I. 45425), Acid Yellow 73 (C.I. 45350), Acid Yellow 3 (C.I. 47005), Acid Green 25 (C.I. 61570), Acid Green 5 (C.I. 42095), Acid Blue S (C.I. 42052), Acid Blue 9 (C.I. 42090), Acid Orange 24 (C.I. 20170), Acid Violet 9 (C.I. 45190), Food Red 6 (C.I. 16155), Acid Red 26 (C.I. 16150), Food Red I (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685), and Brilliant Black 1 (C.I. 28440).

* * * * *